United States Patent

Eufinger et al.

[11] Patent Number: 5,981,812
[45] Date of Patent: Nov. 9, 1999

[54] PROCESS FOR PREPARING α,ω-ALKENOLS

[75] Inventors: Jörg Eufinger, Mülheim; Wilfried Knott; Andreas Mehrwald, both of Essen, all of Germany; Angelo Provinzano, Bottrop, Italy

[73] Assignee: Th. Goldschmidt AG, Essen, Germany

[21] Appl. No.: 08/968,220

[22] Filed: Nov. 12, 1997

[30] Foreign Application Priority Data

Nov. 25, 1996 [DE] Germany ............... 196 48 637

[51] Int. Cl.$^6$ .................................. C07C 29/60
[52] U.S. Cl. ................ 568/903; 568/916; 502/208
[58] Field of Search ................. 568/903, 916, 568/208

[56] References Cited

U.S. PATENT DOCUMENTS 4,250,343  2/1981  Kaufhold et al. ............... 568/903
4,695,661  9/1987  Homann et al. ............... 568/903
5,723,401  3/1998  Sakuma et al. ............... 502/213

FOREIGN PATENT DOCUMENTS 0195 943 B1  10/1986  European Pat. Off. .
29 04518 C2  4/1981  Germany .

OTHER PUBLICATIONS

Thomke et al, Z.Naturforsch,B,27(12),pp. 1462–1464, 1972.

*Primary Examiner*—Shailendra Kumar
*Assistant Examiner*—Sreeni Padmanabhan
*Attorney, Agent, or Firm*—Scully, Scott, Murphy & Presser

[57] ABSTRACT

The invention relates to a process for preparing α,ω-$C_4$–$C_{20}$-alkenols by catalytic monodehydration of α,ω-alkanediols over a catalyst system comprising the combination of aluminum phosphate and barium phosphate. The gas-phase dehydration which occurs over this catalyst at temperatures of from 300 to 500° C. advantageously combines selectivity with a high space-time yield while simultaneously enabling a high throughput over the catalyst.

15 Claims, No Drawings

PROCESS FOR PREPARING α, ω-ALKENOLS

FIELD OF THE INVENTION

The invention relates to a process for preparing α,ω-$C_4$–$C_{20}$-alkenols by cationic gas-phase dehydration of α,ω-alkanediols.

BACKGROUND OF THE INVENTION

According to a process of DE-C-29 04 518, α,ω-$C_4$–$C_{20}$-alkenols having purities of above 85% are synthesized by catalytic dehydration of the corresponding α,ω-$C_4$–$C_{20}$-diols using neutral, simple or mixed pyrophosphates of lithium, sodium strontium or barium or mixtures of these compounds as catalyst. The disadvantage of this process is, on the one hand, the formation of significant proportions of alkanols and, on the other hand, the formation of other by-products increases significantly at conversions of >80% and considerably at conversions of ≧90%.

EP-B-O 195 943 takes up this prior art and teaches a process for preparing pure α,ω-$C_4$–$C_{20}$-alkanols having purities of over 90% by catalytic dehydration of the corresponding α,ω-$C_4$–$C_{20}$-diols, wherein α,ω-$C_4$–$C_{20}$-diols are selectively and partially dehydrated at temperatures of from 300 to 500° C. in the presence of catalysts comprising simple or mixed phosphates of elements of Group II of the Periodic Table doped with alkali metal or alkaline earth metal compounds, where the catalyst is obtained by preparing a catalyst composition by use of alkaline earth metal orthophosphate or alkaline earth metal hydrogen phosphate or by reacting an alkaline earth metal compound with phosphoric acid to give the corresponding phosphate and adding alkali metal or alkaline earth metal compound, if desired shaping this composition, subsequently drying it and then calcining it at temperatures of from 350 to 950° C., to give α,ω-$C_4$–$C_{20}$-alkanols having purities of over 90% at conversions of over 90%.

The catalysts used meet technical requirements in terms of selectivity and operating life, but do not offer a satisfactory solution in terms of the mass throughput, i.e. the effective amount of material which can be passed over the catalyst at a reduced residence time, which is important from a production point of view. The measure frequently employed for the effective throughput over the catalyst is the LHSV, which gives the ratio of starting material flow to catalyst volume. In EP-B-O 195 954, LHSVs of from 0.25 to 0.45 ml/(ml·h) are given for the throughput over the catalyst in the process described.

It is an object of the present invention to achieve a high selectivity linked to a high space-time yield in the gas-phase dehydration of α,ω-alkanediols, specifically 1,6-hexanediol, by selection of a suitable catalyst system.

BRIEF SUMMARY OF THE INVENTION

It has surprisingly been found that a mixed catalyst comprising barium phosphate and aluminum phosphate has both a high catalytic activity and an excellent selectivity.

The invention accordingly provides a process for preparing α,ω-$C_4$–$C_{20}$-alkenols and preferably α,ω-$C_6$ to $C_{14}$ alkenols by catalytic monodehydration of the corresponding alkanediols at temperatures of from 300 to 500° C., wherein the catalyst used is an aluminum phosphate/barium phosphate mixed catalyst.

In this process, the aluminum phosphate/barium phosphate system is used in a molar ratio (aluminum phosphate:barium phosphate) of from 1:10 to 10:1, in particular 1:5 to 5:1.

DETAILED DESCRIPTION OF THE INVENTION

The aluminum phosphate/barium phosphate mixed catalyst used according to the invention can be produced in a manner known per se, e.g. by intensively mixing and compacting aluminum and barium phosphates.

The mixed catalyst can be obtained in a particularly simple way by intensively mixing aluminum phosphate with barium carbonate and then mixing in phosphoric acid, mixing the resulting salt mass with water to improve its moldability, shaping it and then drying and calcining it.

As a deviation from the technical teachings of EP-B-O 195 943, the method of producing the catalyst of the invention is a substantial simplification since it is possible to do without the very particular way of dosing the catalyst constituents at prescribed rates which is necessary in that reference.

The composition of the catalyst of the invention is given by the molar ratio of aluminum phosphate to barium phosphate in the range from 1:10 to 10:1, in particular from 1:5 to 5:1.

Advantageously, the process of the present invention is carried out with water present, preferably in amounts of 10 to 60 wt. %, as a quasi-inert material in the reactant stream. The presence of steam in the catalyzation zone evidently maintains the acid-catalytic activity of the contact and works in addition as a thermal buffer, which promotes the isothermal control of the endothermic elimination. All together the active life of the contact mass employed increases, since undesired background carbonization and cracking processes become lessened.

In the case of water-miscible diols (for example 1,6-hexanediol), one can promote saving the heat of melting the solution of diol in water simply from the receiving vessel in the vaporizer and superheater.

The diols which are not water-soluble are preferably melted in the receiving vessel and then fed to the system, consisting of vaporizer and superheater. The diols which by this time are gaseous can be combined with steam before entry into the reactor.

Fundamentally, an explanation of the process can be imagined as analogous to steam distillation, whereby the diols are obtained with a stream of steam from a vessel in the vaporizer and superheater.

In direct comparison with catalysis as described in EP-B-O 195 943 for dehydrating α,ω-diols, the Ba/Al mixed catalyst used according to the invention is, owing to its high activity, suitable for achieving very short contact times in the reaction zone. Comparative parameters which are not apparatus-specific and are suitable for characterizing the respective catalyst quality are the conversion, the selectivity and the abovementioned LHSV.

Comparison of the gas-phase dehydration of 1,6-hexanediol over catalysts as described in EP-B-O 195 943 and the catalyst system of the invention demonstrates (see Table) that use of the novel catalyst enables the LHSV, as a direct measure of the effective amount of material which can be passed over the catalyst, to be significantly increased while maintaining comparable conversions and selectivities, which is reflected in a considerably increased space-time yield (=mol of product/l of catalyst volume and hour).

This is of tremendous importance for implementing this reaction on an industrial scale, since it allows the operator of the plant to obtain comparable product outputs from significantly smaller reactor volumes.

Production of the aluminum phosphate/barium phosphate mixed catalyst:

EXAMPLE A 230.6 g (2 mol) of 85% strength phosphoric acid were added a little at a time while stirring to 54 g (2 mol) of aluminum grit. After the reaction had abated, the moist salt cake was dewatered for 12 hours at 120° C. in a drying oven. 24.4 g of AlPO$_4$ (0.2 mol) together with 54.4 g (0.28 mol) of barium carbonate were intensively triturated in a mortar and then admixed over a period of 30 minutes with 61.0 g (0.53 mol) of concentrated phosphoric acid. To complete the reaction, 50 ml of water was added. The salt mass obtained was then dried for 30 hours at 120° C.

Before use, the catalyst was calcined for at least 4 hours at 400° C.
Chemical composition:
Al content: 5.3% by weight
Ba content: 37.8% by weight
P content: 23.3% by weight

EXAMPLE B 186 g (2 mol) of concentrated phosphoric acid was added a little at a time while stirring to 54 g (2 mol) of aluminum grit, with a viscous/gelatinous aluminum phosphate AlPO$_4$ being formed in a strongly exothermic reaction with evolution of hydrogen. This material was dewatered for 12 hours at 120° C. in a drying oven.

70.1 g of AlPO$_4$ (0.58 mol) together with 98.5 g (0.5 mol) of BaCO$_3$ were intensively triturated in a mortar and then admixed over a period of 30 minutes with 32.3 g (0.33 mol) of concentrated phosphoric acid. After the reaction was complete, the salt mass was mixed to a paste with water and shaped to form cylindrical rods. The catalyst composition was dried for 30 hours at 120° C.

Before use, the catalyst was calcined for at least 4 hours at 400° C.

| Chemical composition: | | |
|---|---|---|
| Al$_2$O$_3$ content: | 19.90 mol % | 14.79% by weight |
| BaO content: | 27.44 mol % | 30.70% by weight |
| P$_2$O$_5$ content: | 52.65 mol % | 54.50% by weight |
| Physical properties: | | |
| Shape: | extrudates | |
| Specific: | 2.3 m$^2$/g | |
| Bulk density: | 0.966 g/cm$^3$ | |

PRODUCTION EXAMPLES

Example 1

Gas-phase dehydration of 1,6-hexanediol
Description of the Apparatus

In the apparatus for the gas-phase dehydration of 1,6-hexanediol, a glass double-wall dropping funnel heated to 60° C. was used as a reservoir for liquid diol. This reservoir fed a small diaphragm pump having a variable stroke and frequency which conveyed the liquid diol through a spiral tube having a length of 6 m wound between two flanges. Both vaporization and superheating of the starting material take place in this tube. The external diameter of the vaporizer and superheater tube is 4 mm at a wall thickness of 1 mm (D$_i$=2 mm).

The bottom flange of the apparatus rested on a 2 kW laboratory hotplate and conducted the thermal energy directly into the vaporizer and superheater tube. This tube leads to a vertical steel tube (H=80 mm, D$_a$=25 mm, D$_i$—15 mm) which was centered on the flange and served as flow tube reactor. The reactor was filled with the catalyst to be studied in each case. Metal screens fixed on fitting rings at the reactor inlet and outlet limited the maximum height of the catalyst bed to 60 mm.

A downstream condenser condensed and cooled the reaction mixture flowing from the reaction zone and led to an interchangeable receiver for collecting individual fractions. Gaseous low boilers produced were additionally collected in a cold trap cooled by means of acetone/dry ice (−76° C.).

The temperature was measured by means of Ni/Cr—Ni thermocouples installed at the reactor inlet and outlet. A pressure gauge installed downstream of the pump indicated the static pressure in the starting material pipe. If desired, an additional pipe on the pressure side of the pump allows inert gaseous or liquid materials to be fed in.

The reaction zone was electrically heated by means of a heating tape (P$_{e1}$—150 W, T$_{max}$=400° C.) wound around the reactor. To ensure isothermal reaction conditions by avoiding heat losses, the apparatus was insulated with Fibaflax (fibrous aluminum oxide wool) and aluminum foil. These measures allowed the reaction to be carried out isothermally with a maximum temperature difference of 5° K between reactor inlet and outlet. The deviation of the mean temperature from the set value was at most 2° K.

The condensed reaction products collected were analyzed by gas chromatography and also characterized by $^1$H-NMR spectroscopy.
Description of the Experiment The tube reactor was first charged with 10 g of the catalyst from Example 1 and subsequently heated to the desired temperature (450° C.). On reaching a constant temperature, a defined volume flow (1.95 ml/min) of the liquefied starting material (mixture of 80% by weight of hexanediol and 20% by weight of water) in the double-wall dropping funnel was conveyed by means of the metering pump through the vaporizer and superheater tube into the reactor. The temperature was regulated so as to ensure isothermal operating conditions. After leaving the reactor, the gaseous reaction product was condensed in the condenser and the downstream cold trap, collected in the interchangeable receiver and subsequently analyzed by means of gas chromatography and $^1$H-NMR spectroscopy. In the example described, 34% by weight of 5-hexen-1-ol plus 28% by weight of unreacted 1,6-hexanediol were obtained, which corresponds to a selectivity of 77.9 mol % and a conversion of 64.9%. This gives, as a measure of the catalyst output, a space-time yield of 40.28 mol of 5-hexen-1-ol per liter of catalyst volume and hour.

Examples 2 and 3

Using a procedure analogous to Example 1, 1,10-decanediol and 1,8-octanediol were reacted. The results obtained are set forth in the following Table.

Example 4

1,6-Hexanediol was melted in a heated reactor vessel, and then analogously to Example 1 was fed with a constant volume stream of 1.5 ml/minute through a feed pump over vaporizer and superheater to the reactor. The temperature of the reactor was regulated so that the reaction proceeded isothermally.

Gas chromatography and NMR-spectroscopy revealed the parameters shown in the Table.

The experiments emphasize the positive effect of the water fed to the reactant stream (Example 1), since under comparable catalyst charge and nearly identical conversion a lower selectivity is obtained.

TABLE

| Catalyst | Temperature | LHSV ml/(ml.h) | Conversation mol % | Selectivity mol % | Yield % | Space-time mol/(l.h) |
|---|---|---|---|---|---|---|
| B (EP-B-O 195 943) | 380 | 0.29 | 94.8 | 49.5 | 46.9 | 1.20 |
| C (EP-B-O 195 943) | 400 | 0.45 | 49.1 | 55 | 27 | 1.07 |
| II (EP-B-O 195 943) | 440 | 0.25 | 96.2 | 70 | 67.3 | 1.49 |
| Example 1 according to the invention w/1,6-hexanediol | 451 | 9 | 64.9 | 77.9 | 50.6 | 40.28 |
| Example 2 according to the invention w/1,10-decanediol | 460 | 9 | 60 | 48 | 29 | 15.74 |
| Example 3 according to the invention w/1,8-octanediol | 457 | 7.8 | 69 | 62 | 43 | 24.09 |
| Example 4 according to the invention w/1,6-hexanediol | 464 | 9 | 63 | 49.2 | 31 | 24.68 |

What is claimed is:

1. A process for preparing an $\alpha,\omega$-$C_4$–$C_{20}$-alkenol, comprising catalytically monodehydrating the corresponding alkanediol at a temperature of from 300 to 500° C., wherein the catalyst is an aluminum phosphate/barium phosphate mixed catalyst.

2. The process as claimed in claim 1, wherein the aluminum phosphate/barium phosphate catalyst comprises in a molar ratio of aluminum phosphate:barium phosphate of from 1:10 to 10:1.

3. The process as claimed in claim 1, wherein the aluminum phosphate/barium phosphate catalyst comprises in a molar ratio of aluminum phosphate:barium phosphate of from 1:5 to 5:1.

4. The process as claimed in claim 1, wherein prior to said monodehydration, the catalyst is calcined at a temperature of from 400 to 600° C.

5. The process as claimed in claim 2, wherein prior to said monodehydration, the catalyst is calcined at a temperature of from 400 to 600° C.

6. The process as claimed in claim 3, wherein prior to said monodehydration, the catalyst is calcined at a temperature of from 400 to 600° C.

7. The process as claimed in claim 1 wherein the alkanediol which is monodehydrated is in mixture with water.

8. The process as claimed in claim 2 wherein the alkanediol which is monodehydrated is in mixture with water.

9. The process as claimed in claim 3 wherein the alkanediol which is monodehydrated is in mixture with water.

10. The process as claimed in claim 4 wherein the alkanediol which is monodehydrated is in mixture with water.

11. The process as claimed in claim 5 wnerein the alkanediol which is monodehydrated is in mixture with water.

12. The process as claimed in claim 6 wherein the alkanediol which is monodehydrated is in mixture with water.

13. The process of claim 1 where said $\alpha,\omega$-alkenol is 5-hexen-1-ol and said alkanediol is 1,6-hexanediol.

14. The process of claim 1 where said $\alpha,\omega$-alkenol is 7-octen-1-ol and said alkanediol is 1,8-octanediol.

15. The process of claim 1 where said $\alpha,\omega$-alkenol is 9-decen-1-ol and said alkanediol is 1,10-decanediol.

* * * * *